United States Patent [19]
Klippel

[11] Patent Number: 6,005,952
[45] Date of Patent: Dec. 21, 1999

[54] ACTIVE ATTENUATION OF NONLINEAR SOUND

[76] Inventor: Wolfgang Klippel, 326 Longview Pl., Thousand Oaks, Calif. 91360

[21] Appl. No.: 08/416,342

[22] Filed: Apr. 5, 1995

[51] Int. Cl.$^6$ .................................................. A61F 11/06
[52] U.S. Cl. ..................... 381/71.11; 395/22; 381/71.5
[58] Field of Search ................ 381/71, 94; 364/574, 364/148, 1, 151, 724.19, 724.01; 395/22

[56] References Cited

U.S. PATENT DOCUMENTS

| 5,386,689 | 2/1995 | Bozich et al. | 381/71 |
| 5,426,720 | 6/1995 | Bozich et al. | 395/22 |

OTHER PUBLICATIONS

Fuller et al, "A Neural Network Adaptive Controller for Nonlinear Systems", Inter–noise 91, pp. 169–172, 1991.
Cabell et al, "Investigation of Force Distributions for Interior Noise Control Using a Neural Network", Second Conference on Recent Advances in Active Control of Sound and Vibration, pp. 55–69, Apr. 1993.
Brown et al, "An Application of Filtered–x Techniques and Neural Networks to the Active Control of Non–linear Systems", Second Conference on Recent Advcances in Active Control of Sound and Vibration, pp. 3–14, Apr. 1994.

*Primary Examiner*—Curtis Kuntz
*Assistant Examiner*—Ping W. Lee

[57] ABSTRACT

This invention regards a method and an arrangement for attenuating undesirable high amplitude output sound of an acoustic system 2 by injecting a canceling sound produced by a controller 10 and radiated by a loudspeaker 12. The controller 10 has a nonlinear transfer behavior between the control input 20 provided with the sensed input noise and the output 26 connected to the loudspeaker 12. The architecture of the nonlinear controller 10 is directly derived from an acoustic model describing the nonlinear sound propagation in the acoustic system 2. The control architecture can be implemented in a digital signal processor with a minimum of elements and improves the efficiency of the active attenuation so that the fundamental and the nonlinear distortions of the sound can be canceled and the output noise level is lower than by using a linear control system.

22 Claims, 9 Drawing Sheets

ACTIVE ATTENUATION OF NONLINEAR SOUND

FIELD OF THE INVENTION

The present invention relates to acoustic noise reduction systems and more particularly it relates to an electro-acoustic attenuation system utilizing secondary sound for canceling unwanted primary sound. The invention discloses a control system with a nonlinear transfer characteristic to compensate for nonlinear distortion caused by the primary and secondary sound propagating nonlinearly at high sound pressure levels.

BACKGROUND OF THE INVENTION

Active acoustic attenuation involves injecting a secondary sound to destructively interfere with and cancel a primary sound. Describing the primary sound by the unwanted pressure fluctuation $p_P(x, t)$) then the secondary pressure fluctuation $p_s(x, t)$ has to be equal in magnitude and in opposite phase (180°), to obtain a total pressure fluctuation $p(x,t)=p_s(x, t)+p_P(x, t)=0$. The generation of the required secondary sound requires an accurate model of the transformation that the primary sound undergoes as it propagates along the path to the source of the secondary sound.

DISCUSSION OF RELATED KNOWN ART

The related art of active acoustic attenuation is restricted to applications where the sound pressure is rather small and a linear sound propagation can be assumed. Therefore, the secondary sound can be produced by a controller with a linear transfer response as disclosed in the early U.S. Pat. No. 2,043,416 to Lueg, U.S. Pat. No. 4,122,303 to Chaplin, U.S. Pat. No. 4,473,906 to Warnaka et al. and more recent patents U.S. Pat. No. 5,172,416 to Allie et. al., U.S. Pat. No. 5,278,913 to Delfosse et al.

Only in a linear system the principle of superposition is valid which is considered essential to active sound control as Nelson and Elliot stated in the book *Active Control of Sound*, Academic Press, London 1992 that "it is the principle of superposition that enables the active control of sound to be accomplished".

However, in some applications of active noise attenuation (e.g. in mufflers, jets turbines) the pressure of the primary sound is so high that the nonlinearity of the air has to be taken into account. Typically, a sinusoidal sound wave of 500 Hz propagating in a duct at a sound pressure level L=140 dB generates harmonic distortion of about 1% after traveling a distance of 1 m. These distortions cause the characteristic steepening of the propagating wave front and result finally in a formation of a shock wave. They can not be attenuated by a linear control system as used in related art.

Though active attenuation of nonlinear sound is considered as not possible in related art, controllers with a nonlinear transfer characteristic were proposed for the active attenuation of vibration on mechanic structures. The proposed nonlinear controllers have a generic structure using polynomial filters or artificial neural networks. C. H. Fuller, et. al. proposed "A Neural Network Adaptive Controller for Nonlinear Systems", Proceedings Inter-Noise 1991 p. 169–172. Recent works from D. E. Brown, et. al.: "An Application of Filtered-x Techniques and Neural Networks to the Active Control of Non-Linear Systems", R. H. Cabell, et. al.: "Investigation of Force Distributions for Interior Noise Control Using a Neural Network" and L. Lecce, et. al: "Estimation of the Dynamic Behavior of Complex Structures by Neural Networks", all three papers presented at the Second Conference on Recent Advances in Active Control of Sound and Vibration, Virginia Polytechnic Institute and State University Blacksburg, Va., Apr. 28–30, 1993, Technomic Publishing Com, Lanchester show a first formal approach in controlling nonlinear systems with neural networks.

Neural networks offer new possibilities in the control of multi-channel systems, in the adaptive adjustment of the network and in compensating nonlinear mechanisms in the plant but the main benefit of using networks is that with a minimum of information about the physics in the plant, a nonlinear controller can be realized. That is important in applications where the nonlinear mechanisms in the plant are very complex and an adequate model can not be established.

At present, the application of neural networks and other generic nonlinear filters is difficult because their implementation requires a large amount of processing capacity and the convergence of an adaptive parameter adjustment is generally slow.

The generic nonlinear control architectures used in related art do not consider the specific mechanisms of nonlinear sound propagation in an acoustic system. For instance, the sound wave injected by the loudspeaker in upstream direction is fed back to the controller input and can only be compensated by a recursive controller structure with an infinite impulse response. The controller in "A Neural Network Adaptive Controller for Nonlinear Systems", disclosed by C. H. Fuller, et. al. in Proceedings Inter-Noise 1991 p. 169–172 has only a finite impulse response and the secondary sound generated by this controller can not cancel the input noise completely.

There is thus a need for an active acoustic attenuation system which is able to cope with nonlinear sound propagation and can be realized with existing electronic components.

OBJECTS OF THE INVENTION

It is a primary object of the present invention to provide active attenuation having improved efficiency so that the nonlinear distortions generated in the primary sound can be canceled and the remaining noise level is lower than by using a linear controller of related art.

Another object is to realize an active attenuation system for high amplitude sound comprising a minimum of elements and requiring a minimum of processing capacity in a digital signal processor (DSP) to keep the cost of this system low.

A further object is to provide an active attenuation system which has a minimum of unknown controller parameters which can be easily adjusted.

SUMMARY OF THE INVENTION

A nonlinear control architecture is directly derived from a model describing the nonlinear sound propagation in the acoustic system so that the secondary sound radiated by the loudspeaker cancels the input noise and thus attenuates the output noise. In a first embodiment a ladder filter models the nonlinear propagation of the input sound and of the secondary sound and their nonlinear interferences. Additional filters at the input and output of the controller compensate for the linear and nonlinear transfer behavior of the microphone and loudspeaker sensing the input sound and injecting the canceling sound, respectively. Further embodiments with a simplified control architectures are derived from higher-order system functions which describe the nonlinear overall relationship between the sound pressure at two points in the sound field. The higher-order system functions reveal that nonlinear filters with a $S_M$-structure used in a feed-forward and a feedback path are adequate to model the nonlinear sound propagation in the acoustic system and to synthesize a secondary sound which cancels the distorted input sound. The disclosed embodiments of the nonlinear controller can be easily realized by using dynamic linear systems (filters, delay elements) and static nonlinearities (diode networks, multipliers, a neural network).

BRIEF DESCRIPTION OF THE DRAWINGS

The above and further objects, features and advantages of the present invention will be more fully understood from the following description taken with the accompanying drawings in which.

DETAILED DESCRIPTION

Related Art

Figure 1:
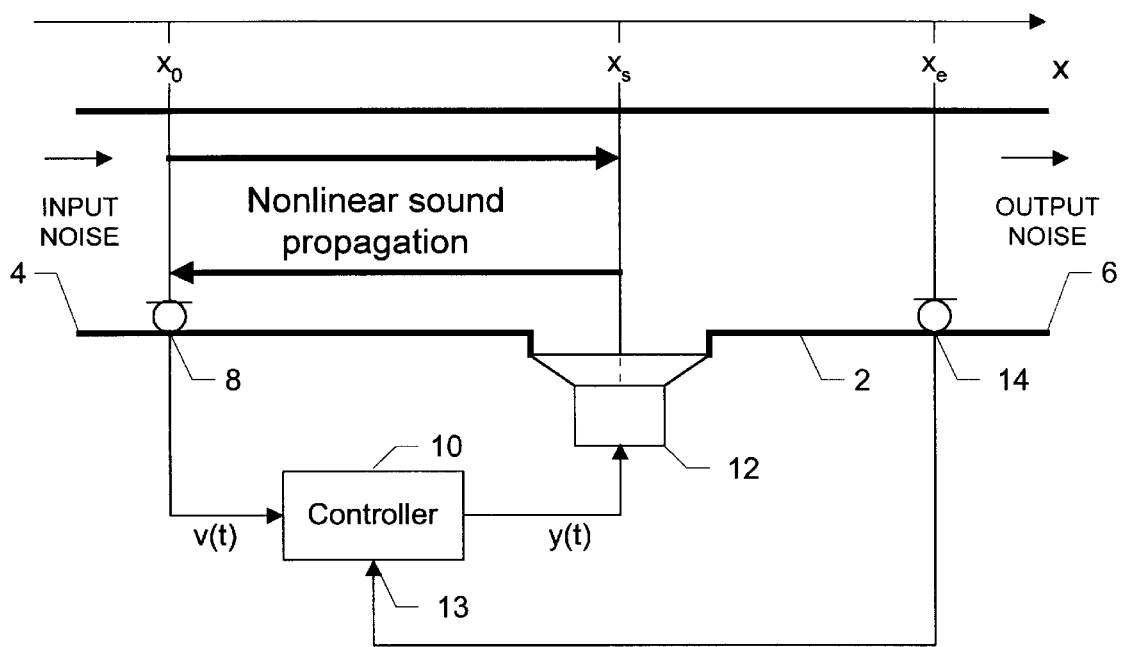
FIG. 1 is a schematic illustration of an active acoustic attenuation system known in the related art.

FIG. 1 shows a known related art attenuation system comprising an acoustic system such as a duct 2 having an input 4 for receiving input noise and an output 6 for radiating output noise. The input noise at point $x_0$ is sensed with an input microphone 8 and an input signal v(t) is sent via controller 10 to a loudspeaker 12. The loudspeaker 12 injects canceling sound into the duct 2 which sound is optimally equal in amplitude and opposite in phase to the downstream traveling input noise at point $x_s$ to thus cancel same. The superimposed downstream traveling noise is sensed at point $x_c$ and the output of the microphone 14 is supplied as an error signal to the control input 13 to adjust the controller 10 adaptively.

Figure 2:
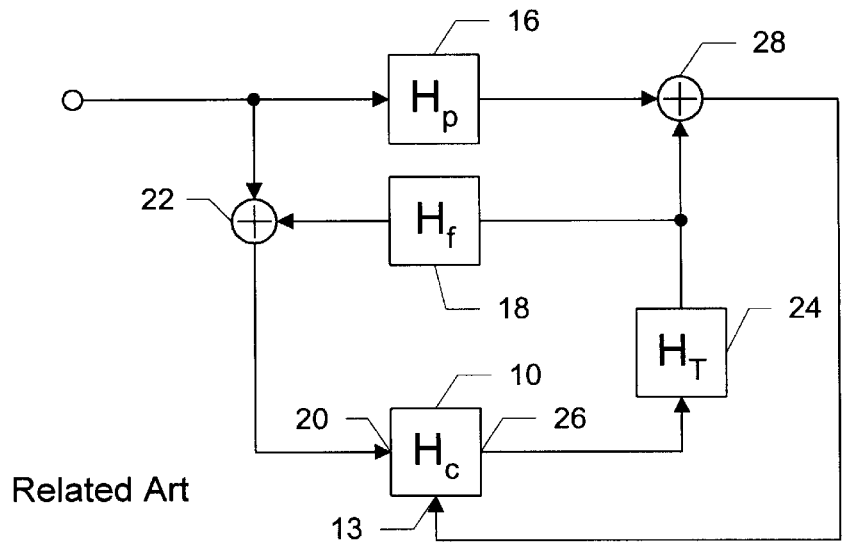
FIG. 2 is a block diagram modeling the related art system of FIG. 1.

FIG. 2 shows the signal flow block diagram of the active attenuation system in related art corresponding to FIG. 1. The relationship between the input noise at point $x_0$ and the output signal of the microphone 14 is described by the linear system 16. The transfer characteristic from the output 26 of the controller 10 via loudspeaker 12 to the output of the microphone 14 is modeled by the linear system 24. The propagation of the feedback noise radiated by the loudspeaker 12 in upstream direction is modeled by the linear system 18. The summer 22 corresponds with the microphone 8 which senses the sum of the downstream and upstream traveling waves and provides the signal v(t) for the input 20 of controller 10. The output signal of summer 28 is the output noise measured by microphone 14 and supplied as an error signal to the control input 13.

Because the propagation of the sound in the duct is modeled by a linear system, the required secondary sound is produced by a controller 10 with a linear transfer characteristic. U.S. Pat. No. 4,677,677 to Eriksson discloses an infinite impulse response filter (IIR) which is used to adaptively model the linear system 16 and linear system 18.

However, at high sound pressure amplitudes, the propagation of the downstream and upstream travelling waves becomes nonlinear and linear system modeling is not adequate. Additional nonlinear distortions are produced in the downstream signal which are not canceled by the secondary sound provided by the linear controller 10. The upstream traveling sound is also contaminated by nonlinear distortion so that the feedback path compensation in the controller is not complete. If the loudspeaker 12 is not directly mounted to the duct 2 but there is an additional connection duct (transmission line, horn, phase forming device) between the loudspeaker's diaphragm and the duct 2 the high level canceling sound radiated by loudspeaker 12 is also affected by nonlinear wave steepening.

There is a need for a controller with a nonlinear transfer characteristic to cope with the effects of nonlinear sound propagation inside the acoustic system.

Present Invention

Figure 3:
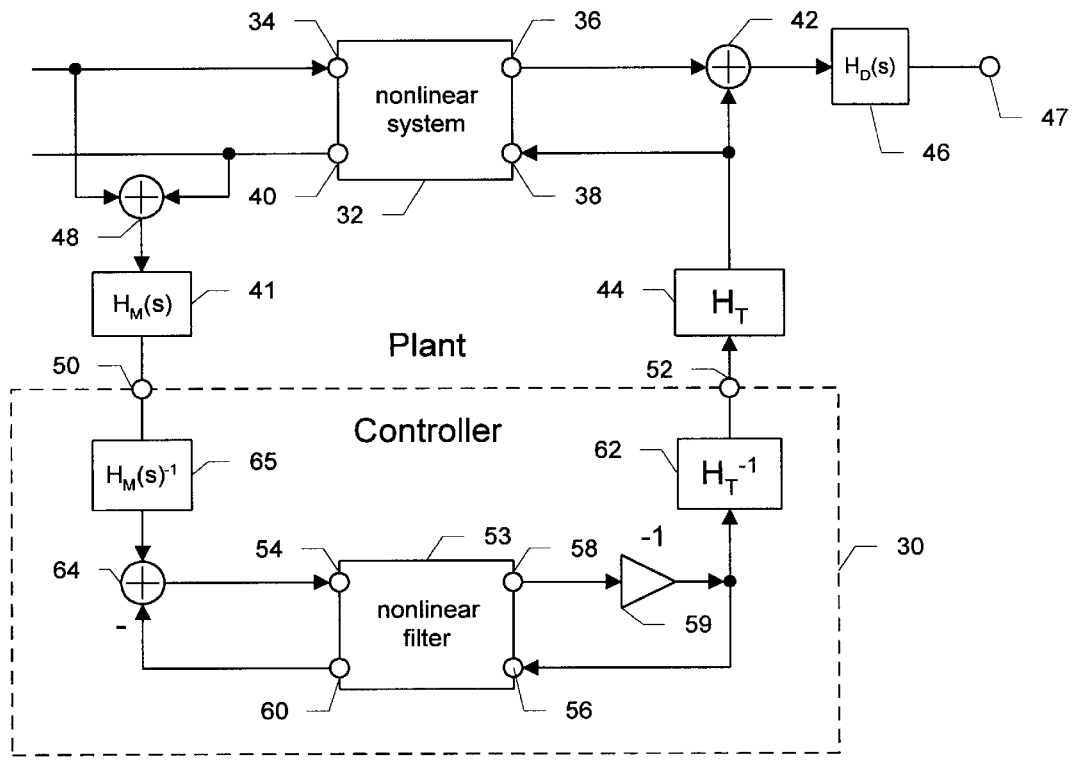
FIG. 3 is a first embodiment of an active noise attenuation system in accordance with the present invention.

FIG. 3 is a first embodiment of the active attenuation system in accordance with the invention. This block diagram is also based on the schematic illustration of the active attenuation system depicted in FIG. 1 but the linear control system 10 is replaced by a nonlinear controller 30. The propagation of the downstream and upstream travelling waves is modeled by a nonlinear system 32. This system 32 has an input 34 and an output 36 for the downstream travelling wave and another input 38 and another output 40 for the upstream travelling wave. In contrast to the linear modeling in FIG. 2 the signals at the outputs 36 and 40 depend on a nonlinear relationship from the input signals at 34 and 38. The input noise $p^f(x_0, t)$ at the input 34 of the nonlinear system 32 generates a signal $p^f(x_s, t)$ at output 36. At point $x_s$ the secondary sound $p_s(t)$ radiated by the loudspeaker 12 meets the downstream traveling sound $p^f(x_s, t)$. The summer 42 describes the superposition of the primary sound $p^f(x_s, t)$ and the secondary sound $p_s(t)$. The system 44 describes the relationship between the electric signal y(t) at the output 52 of the controller 30 and the sound pressure signal $p_s(t)$. This system is nonlinear if the nonlinearities of the loudspeaker 12 and the nonlinear sound propagation between the loudspeaker's diaphragm and the point $x_s$ in the duct 2 are considered.

The downstream propagation of the superimposed signal from point $x_s$ to point $x_c$ is modeled by a linear system 46 with the transfer function $H_D(s)$ because the amplitude of the attenuated noise is low and linear sound propagation can be assumed. The feedback noise $p^b(x_s, t)$ radiated from loudspeaker 12 in upstream direction is the input 38 of the nonlinear system 32. The upstream signal $p^b(x_0, t)$ at the output 40 is added with the input noise $p^f(x_0, t)$ by summer 48 and the total sound signal $p(x_0, t)$ is filtered by the linear system 41 with the transfer response $H_M(s)$ to consider the transfer behavior of the microphone 8. The output of the system 41 is supplied to the controller input 50.

The nonlinear controller 30 contains a nonlinear filter 53 with two inputs 54, 56 and two outputs 58, 60. The output 58 providing the downstream traveling noise $p^f(x_s, t)$ is connected via a inverter 59 both with the input 56 and via the filter 62 with the output 52 of the controller 30. The inverter 59 changes the phase of all signal components by 180° and provides a signal $p_s(t)$ which is the required secondary sound $p_s(t)$. The filter 62 has the inverse transfer response of the system 44 to ensure that the output signal of the inverter 59 is identical with the secondary sound $p_s(t)$ at the point $x_s$ in the duct 2. The filter 62 can contain the nonlinear compensation filter as proposed in U.S. patent application Ser. No. 07/867,314 to Klippel entitled "Arrangement to correct the Linear and Nonlinear Transfer Behavior of Electro-Acoustical Transducer" to compensate for nonlinearities of the transducer.

The compensation of the upstream travelling noise $p^b(x_0, t)$ is accomplished by the summer 64 which has an inverting and an noninverting input. The controller input signal v(t) is supplied via the linear filter 65 to the non-inverting input of summer 64. The linear filter 65 has the inverted microphone response $H_M(s)^{-1}$. The downstream propagating signal $p_b(X_0, t)$ at output 60 is supplied to the inverting input of summer 64. The output signal $p^f(x_0, t) = p(x_0, t) - p_b(x_0, t)$ of summer 64 is the reconstructed input noise and is supplied to the input 54 of the nonlinear filter 53.

If the nonlinear filter 53 has the same transfer characteristic as the nonlinear system 32 and the filters 62 and 65 have the inverse transfer characteristic of the system 44 and 41, respectively, then the signal at the filter input 54 is identical to the input noise at the input 34 of the nonlinear system 32 and the signal $p_s(t)$ at the output of system 44 cancels the noise $p^f(x_s, t)$ of output 36 completely.

The design of the filter 53 and filter 62 in the controller 30 is based on an extended model of the nonlinear sound propagation in system 32 and 44. A priori knowledge about the physical mechanisms in the plant will be used to select the most efficient filter structure.

Basic investigations of the nonlinear propagation in ducts and horns were performed by S. Goldstein et. al., "Sound Waves of Finite Amplitude in an Exponential Horn," J. Acoust. Soc. Am., vol. 6, pp. 275–278 (April 1935) and L. J. Black, "A Physical Analysis of Distortion Produced by the Nonlinearity of the Medium," J. Acoust. Soc. Am. 12, 266–267 (1940). In a more recent publication by W. Klippel, "Nichtlineare Wellenausbreitung in Hörnern," 20. Tagung der Deutschen Arbeitsgemeinschaft für Akustik (DAGA '94), Dresden (1994), In: Tagungsband Fortschritte der Akustik, a transmission line model was derived from the one-dimensional differential equation based on Lagrangian coordinates. The law of conservation of mass and the gas law lead to the following nonlinear partial differential equation $$\frac{\partial q}{\partial x} = -\frac{S}{p_0 \gamma} \frac{\partial p}{\partial t} + SN(p)\frac{\partial p}{\partial t} \qquad (1)$$

using the volume velocity q, the sound pressure p, the static air pressure $p_o$ and the adiabatic constant $\gamma=1.4$, the mean cross-sectional area S(x) and the distributed compliance parameter $$N(p) = \frac{1}{\gamma P_0} - \frac{1}{\gamma p_0}\left(\frac{p+p_0}{p_0}\right)^{-\frac{\gamma+1}{\gamma}} \approx \frac{(\gamma+1)}{(\gamma p_0)^2}p - \frac{(\gamma+1)(2\gamma+1)}{2(\gamma p_0)^3}p^2 \qquad (2)$$

which is approximated by a Taylor-series expansion truncated after the second-order term. The product of N(p) with the time derivation of p, the last term in Eq. (1), shows that over a small distance of $\partial x$ a distortion component is added to the volume velocity q.

The second equation $$\frac{\partial q}{\partial t} = -\frac{S}{\rho_0}\frac{\partial p}{\partial x} \qquad (3)$$

results from Newton's Law and describes the displacement of an air element with the density $\rho_o$ without any dissipation. The partial differential Eqs. (1) and (3) describe the relationship between volume velocity q and sound pressure p in an infinite small section of the duct.

Figure 4:
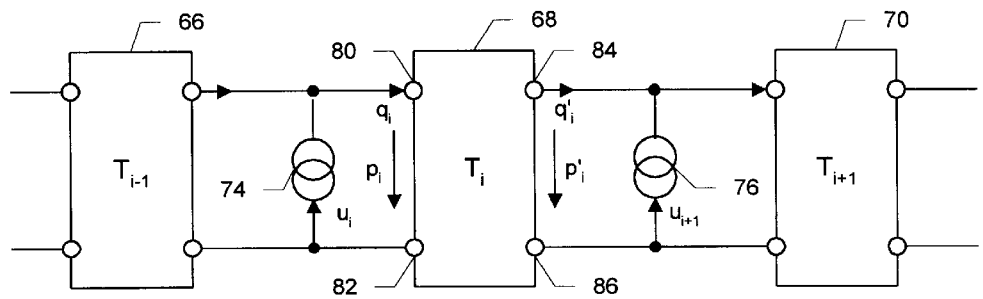
FIG. 4 is a transmission line model representing the nonlinear sound propagation.

Increasing the width $\partial x$ of the section to finite value L and interpreting Eqs. (1) and (3) as difference equations leads to a transmission line model with discrete acoustical elements as shown in FIG. 4. The nonlinear mechanisms are separated from the linear propagation. The transmission and reflection of the downstream and upstream traveling waves is described by linear four-ports connected in series. Only three four-ports 66, 68, 70 are shown in FIG. 4. The ith four-port 68, representing all the other four-ports, is characterized by the volume velocity $q_i$ and pressure $p_i$ at the upstream ports 80, 82 and by the volume velocity $q_i'$ and pressure $p_i'$ at the downstream ports 84, 86. The relationship $$\begin{bmatrix} P_i'(\omega) \\ Q_i'(\omega) \end{bmatrix} = T_i(\omega)\begin{bmatrix} P_i(\omega) \\ Q_i(\omega) \end{bmatrix} \qquad (4)$$

between the Fourier-transformed velocities $Q_i'(\omega)$, $Q_i(\omega)$ and sound pressures $P_i'(\omega)$, $P_i(\omega)$ at both sides of the four-port can be described by a transfer matrix $T_i(\omega)$. This transfer matrix can be specified if an exponential, cylindrical or conical change of the cross-sectional area of the section is assumed. For a cylindrical section the transfer matrix $$T_i(\omega) = \begin{vmatrix} \cos\left(\frac{\omega L}{c}\right) & \frac{j\rho_0 c}{S_i}\sin\left(\omega\frac{L}{c}\right) \\ \frac{jS_i}{\rho_0 c}\sin\left(\omega\frac{L}{c}\right) & \cos\left(\omega\frac{L}{c}\right) \end{vmatrix} \quad (5)$$

corresponds with the cross-sectional area $S_i$ and the width L of the section as described in detail in D. Mapes-Riordan, "Horn Modeling with Conical and Cylindrical Transmission-Line Elements," J. Audio Eng. Soc., Vol. 41, No. 6, 1993 June, pp. 471–484.

The nonlinearity is concentrated in additional sources of volume velocity represented by elements 74 and 76 in FIG. 4. The source 74 supplies a volume velocity $$u_i t(p_i) = S_i L N(p_i) \frac{dp_i}{dt} \quad (6)$$

into the transmission line where N(p) is given in Eq. (2). This additional volume velocity can be interpreted as nonlinear distortions which travel in both directions of the duct.

The distortion wave which travels in the same direction as the fundamental wave accumulates in magnitude. The accumulation occurs because the arriving wave controls the distortion generation in every section and the distortion components add as they are in phase. The generation of the higher-order distortion is caused by the series connection of sections with low-order nonlinearities. The low-order distortions generated in previous sections cause high-order distortions in the following sections.

Figure 5:
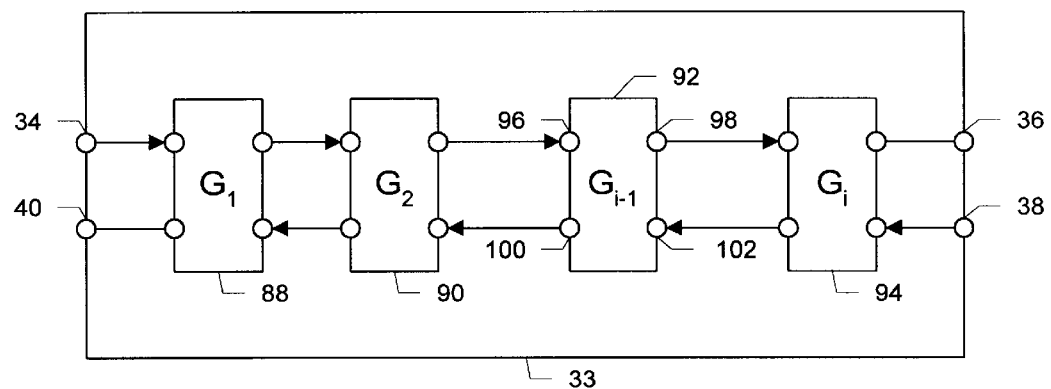
FIG. 5 shows a ladder filter used both as a model of the nonlinear sound propagation and as an embodiment of the nonlinear filter in the controller of FIG. 3.

The transmission line shows the instantaneous total sound pressure and total volume velocity at every section. Considering the downstream and upstream traveling sound parts the transmission line model can be transformed into a signal flow chart with a ladder structure as shown in FIG. 5. This ladder structure 33 corresponds with the nonlinear system 32 and is an embodiment of the nonlinear filter 53 in FIG. 3. It has the input 34 for the input noise $p^f(x_0, t)$ the output 36 for the downstream traveling sound $p^f(x_s, t)$ and the input 38 and output 40 for the upstream traveling noise $p^b(x_s, t)$ and $p^b(x_0, t)$, respectively. The ladder structure 33 comprises nonlinear subsystems 88, 90, 92, 94 which have the same structure and perform the transmission, reflection of the sound waves and the generation of nonlinear distortions in every section. The subsystem 92 as the other subsystems comprises an input 96 and an output 98 for the downstream travelling sound and an input 102 and an output 100 for the upstream travelling sound.

Figure 6:
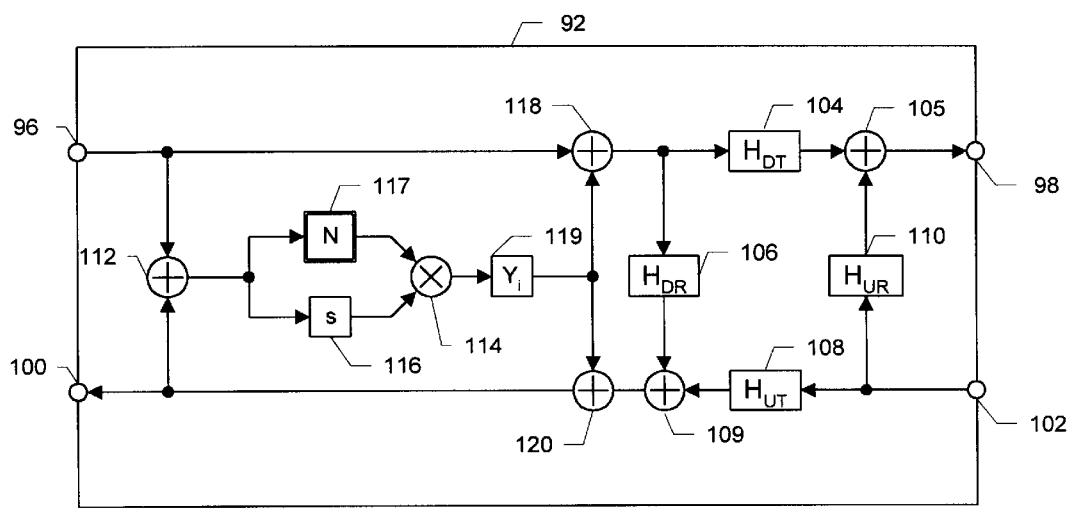
FIG. 6 shows a section of the ladder filter of FIG. 5 in greater detail.

FIG. 6 shows the system structure of the subsystem 92 in greater detail and represents all the other subsystems in the ladder structure. It contains a linear part which describes the linear propagation of the sound waves and a nonlinear part which generates the nonlinear distortion. The downstream traveling wave is partly transmitted via the linear filter 104 to the next downstream section and partly reflected via the linear filter 106, respectively. The linear filters 108 and 110 perform the transmission and reflection of the upstream traveling wave, respectively. The reflected and transmitted sound waves are added by the summers 105 in the downstream path and by summer 109 in the upstream path. The nonlinear part contains a summer 112 which provides the total sound pressure via the static nonlinear system 117 to the first input of multiplier 114 and via the differentiator 116 to the second input of multiplier 114. The relation between the input and output of the static nonlinear system 117 is described by Eq. (2). The nonlinear distortions generated at the output of multiplier 114 are filtered by the linear system 119 and then added by summers 118 and 120 to the upstream and downstream travelling waves. For a cylindrical section the transfer function of the linear system 119 is the product of width L with the specific acoustic impedance $Z_i(s)=\rho c$ of an infinite tube.

FIG. 5 and FIG. 6 represent not only a system model of the nonlinear sound propagation in system 32 in FIG. 3 but can also be used as an embodiment of the nonlinear filter 53 in the controller 30. However, it is useful to simplify this ladder filter to facilitate the practical implementation.

Figure 7:
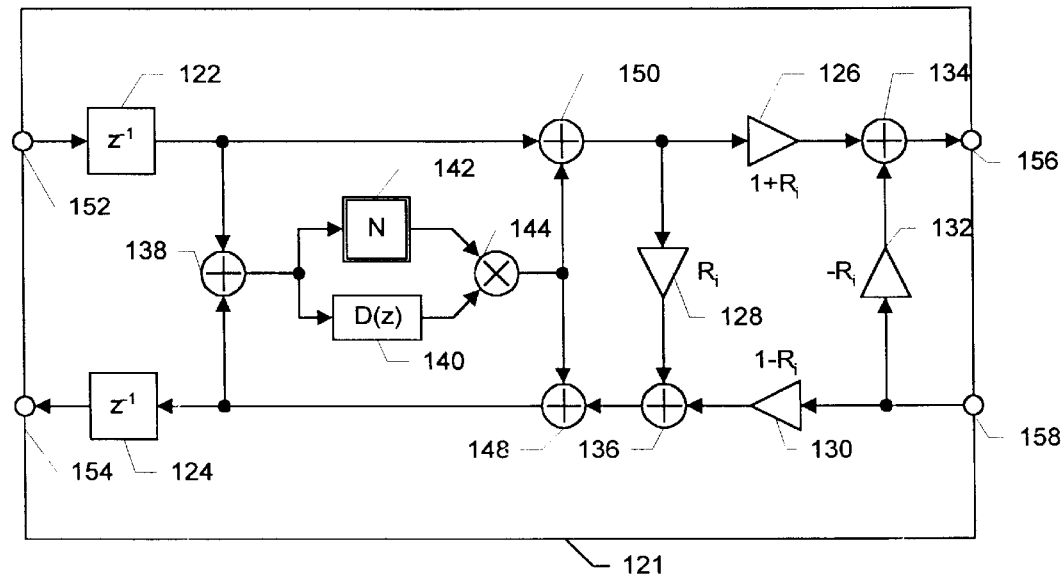
FIG. 7 shows an embodiment of each filter section of FIG. 5 in the discrete time domain.

Modeling the duct 2 by a transmission line composed of cascaded cylinders of differing diameter and equal length leads to a discrete time filter 121 as presented in FIG. 7. Filter 121 represents all the other filters in the cascaded ladder structure 33 in FIG. 5. The inputs 152 and 158 and outputs 156 and 154 correspond with the inputs 96 and 102 and outputs 98 and 100 of subsystem 92, respectively. However, the upstream and downstream traveling sound pressure waves are sampled at discrete times and are represented by sequences $p^f[x_i, n]$ and $p^b[x_i, n]$. Assuming plane waves in the acoustic system, the specific acoustic impedance $Z_i(s)=\rho c$ is independent of frequency and therefore the reflection and transmission of the wave can be modeled by amplifiers 126, 128, 130, 132 and summers 134, 136. The propagation time $\tau=L/c$, required for the wave to travel with the speed c through he section with the length L, is represented by additional delay elements 122, 124. The gain of the amplifier 132 is $-R_i$, the gain of 130 is equal to $1-R_i$, the gain of 128 is $R_i$ and the gain of 126 is $1+R_i$ with $$R_i = \frac{S_i - S_{i+1}}{S_i + S_{i+1}} \quad (7)$$

and the cross-sectional areas $S_i$ and $S_{i+1}$ at the junction between section i and section i+1. The ideal differentiator 116 and the linear filter 119 is replaced by a FIR filter 140 with a short response $D(z)=\alpha(1-z^{-1})$. The static nonlinear system 142 corresponds with Eq. (2). The output signals from the static nonlinearity 142 and the linear FIR-filter 140 are multiplied by multiplier 144 and the product signal is added by summer 150 and 148 to the downstream sequence and to the upstream sequence, respectively.

The embodiment shown in FIG. 5 using FIG. 6 or FIG. 7 can be implemented in a time discrete signal processor (DSP). The number of the required elements (adder, scaling units and time-delay elements) can be reduced by making the length L of one section as large as possible under consideration of the variation of the cross-sectional areas of the duct 2. In many practical cases the duct has a constant diameter and the reflections of the sound in the duct are negligible.

Figure 8:
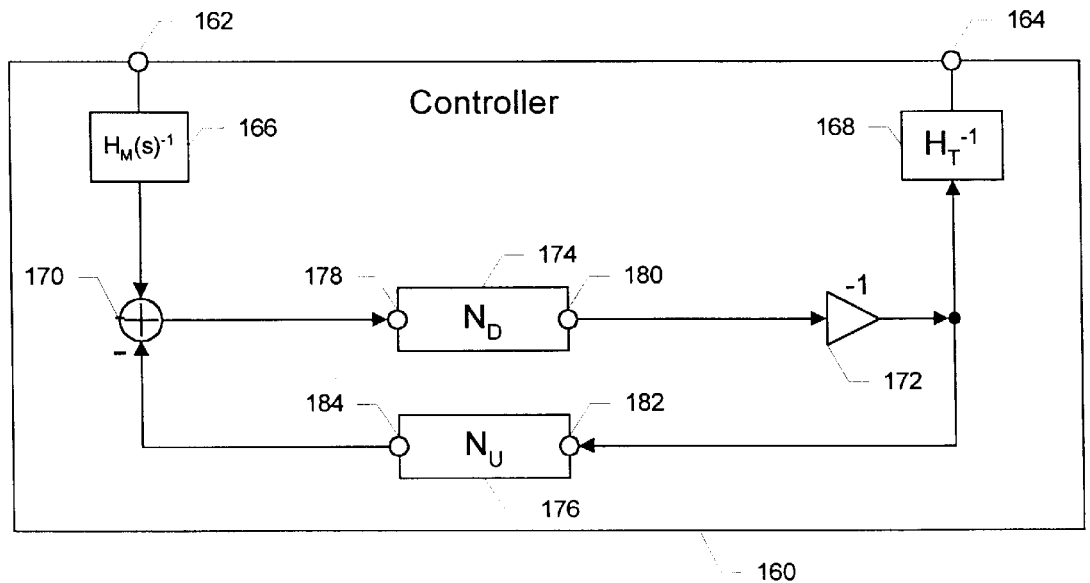
FIG. 8 shows a second embodiment of the nonlinear controller.

FIG. 8 shows a second embodiment of the invention. The controller 160 is based on a simplified model of the nonlinear sound propagation in the acoustic system and replaces controller 30 in FIG. 3. Interactions between the downstream and upstream travelling waves in the system 32 are neglected. The nonlinear filter 53 in FIG. 3 is replaced by two nonlinear filters 174 and 176 which are separately connected in the downstream and upstream path. The input 162, the output 164, the filters 166 and 168, the summer 170 and the inverter 172 correspond with the elements 50, 52, 65, 62, 64, 59 shown in FIG. 3, respectively. The output of the summer 170 is connected via input 178 and output 180 of the nonlinear filter 174 with the input of the inverter 172. The output of the inverter 172 is connected via input 182 and output 184 of the nonlinear filter 176 with the inverting input of the summer 170.

The overall response of the downstream path between input 34 and output 36, the upstream path between input 38 and output 40 and the nonlinear sound propagation from loudspeaker's diaphragm to the point $x_s$ are described by higher-order system functions based on VOLTERRA-series expansion. The first-order system function $$H_1(s) = \exp\left\{-\frac{sd}{c}\right\} \tag{8}$$

the second-order system function $$H_2(s_1, s_2) = \frac{n_1 \rho_0 cd}{4}(s_1 + s_2)\exp\{-(s_1 + s_2)d/c\} \tag{9}$$

and third-order system function $$H_3(s_1, s_2, s_3) = \left\{\frac{(n_1\rho_0 cd)^2}{12}(s_1 + s_2 + s_3)^2 + \frac{n_2\rho cd}{6}(s_1 + s_2 + s_3)\right\} \times \tag{10}$$

$$\exp\{-(s_1 + s_2 + s_3)d/c\}$$

describe the nonlinear propagation of a plane wave over a distance d.

Figure 9:
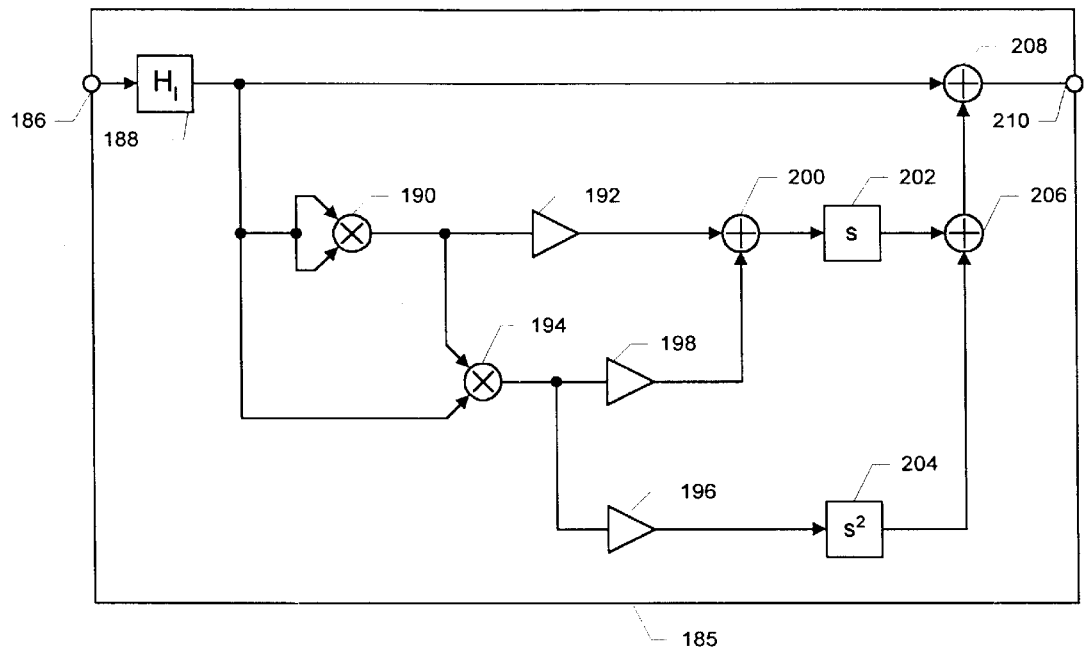
FIG. 9 shows a nonlinear filter which describes the nonlinear sound propagation of a plane wave between two points of the sound field.

FIG. 9 shows a nonlinear filter 185 which realizes the system functions in Eqs. (8), (9) and (10) by using dynamic linear and static nonlinear elements. The input 186 is connected with the input of a linear filter 188 which describes the linear sound propagation of a plane wave between two points of the sound field. The output of the linear filter 188 is connected with the first input of adder 208 and with the input of a squarer 190 and with the input of a third-order power device realized by squarer 190 and multiplier 194. The outputs of the squarer 190 and the multiplier 194 are connected via amplifiers 192 and 198, respectively, with summer 200. The output of the summer 200 is supplied to a first-order differentiator 202. The output of the multiplier 194 is also connected via amplifier 196 with a second-order differentiator 204. The output signals of both differentiators 202 and 204 are added by summers 206, 208 with the linear signal and supplied to the output 210 of the filter 185.

The nonlinear filter 185 describes not only the nonlinear sound propagation in the system 32 and 44 but can also used as an effective embodiment of the nonlinear filters 174, 176 and 168 in FIG. 8. Whereas the filter 174 and 176 simulate the nonlinear sound propagation in system 32, the filter 168 has the inverse transfer characteristic of the system 44. The nonlinear wave propagation between loudspeaker's diaphragm and the point, where the secondary sound meets the primary sound, has to be compensated by a predistorted controller output signal. Using the architecture of filter 185 to realize filter 168 and changing the sign of the gain in the amplifiers 192, 196, 198 allow to synthesize nonlinear distortions which are equal in amplitude but 180°-phase shifted to the distortions caused by wave steepening.

Figure 10:
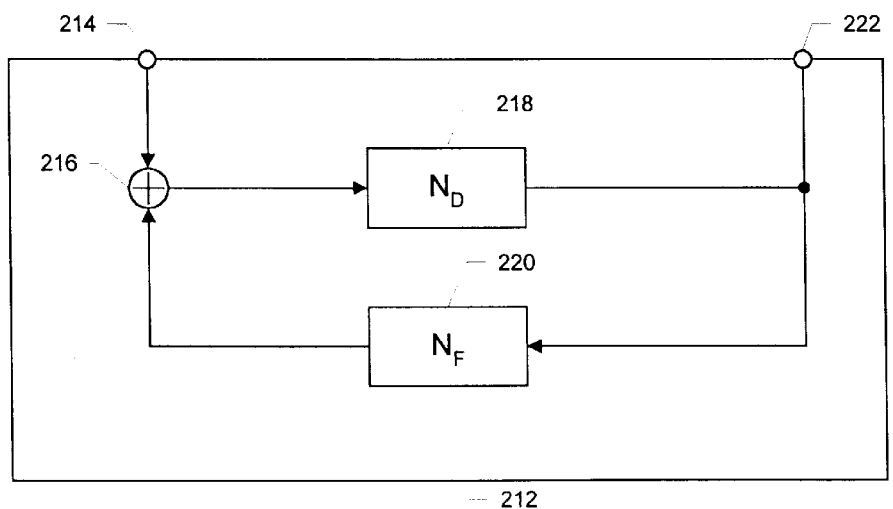
FIG. 10 shows a third embodiment of the nonlinear controller where the filters with the inverse loudspeaker and microphone response are combined with the nonlinear filters describing the nonlinear sound propagation.

FIG. 10 shows a third embodiment of the invention. The nonlinear controller 212 corresponds with controller 160 in FIG. 8 but the filters 166 and 168 and the phase inverter 172 are combined with the nonlinear filters 174 and 176. The input 214 of controller 212 is connected to the first input of a summer 216 and the output of summer 216 is connected via a first nonlinear filter 218 with the output 222 of the controller 212. The output of the nonlinear filter 218 is also connected via a second nonlinear filter 220 with the other input of summer 216. Each nonlinear filter 218 and 220 can be realized by further subfilters which are connected in parallel or in series.

Figure 11:
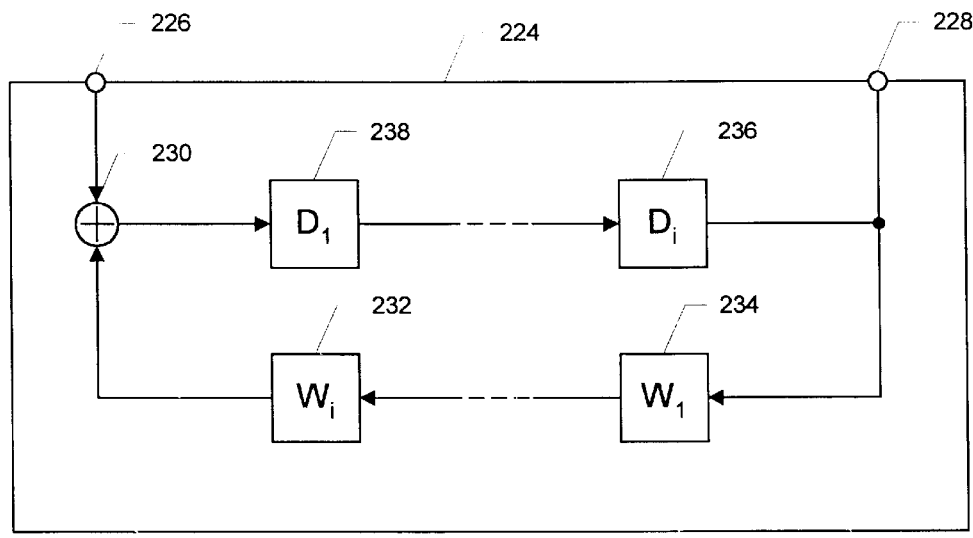
FIG. 11 shows the controller of FIG. 10 wherein each nonlinear filter comprises nonlinear subfilters connected in series.

FIG. 11 shows a special embodiment 224 of the controller 212 in FIG. 10. Both nonlinear filters 218 and 220 are replaced by a series of nonlinear subfilters. FIG. 11 shows only two subsystems 238, 236 in the downstream path and two subfilters 232, 234 in the upstream path. The input 226, the output 228 and summer 230 correspond with the elements 214, 222 and 216 in FIG. 10, respectively.

If the amplitude of the feedback sound radiated from loudspeaker 12 in upstream direction is negligible, the nonlinear subfilters 232, 234 and the summer 230 in the feedback compensation of FIG. 11 can be omitted and the remaining cascade of nonlinear subfilter 238 and 236 replaces the nonlinear controller 30 in in FIG. 3.

Figure 12:
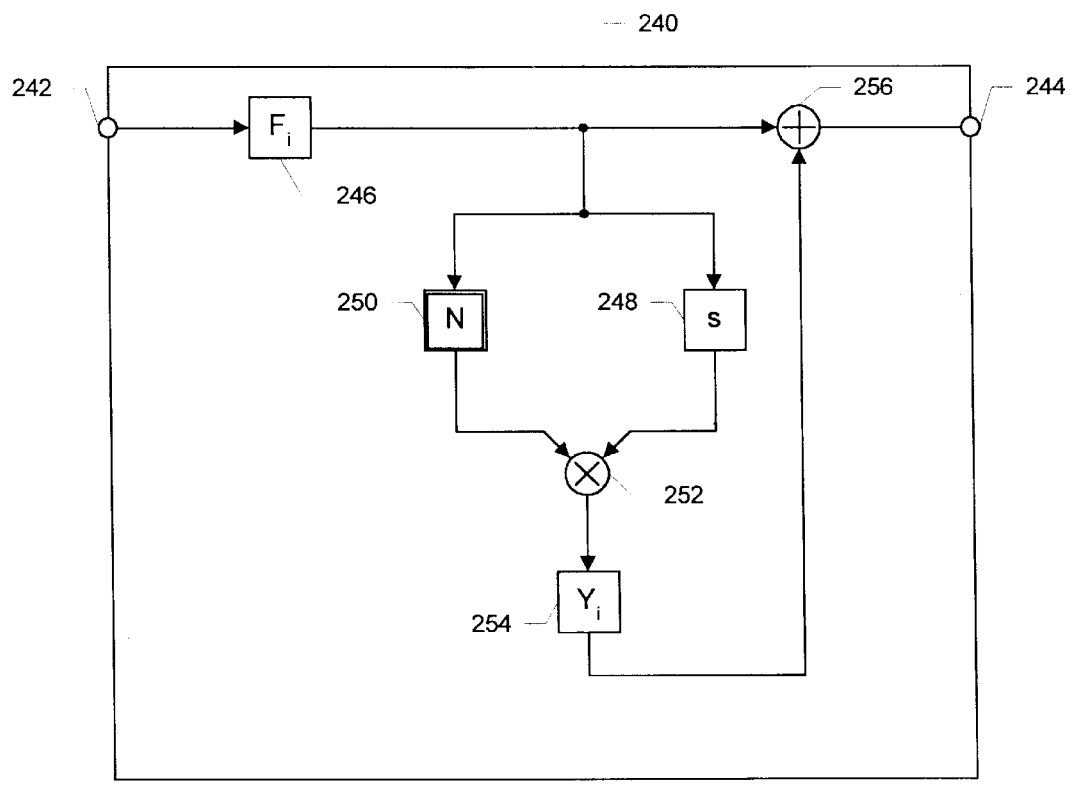
FIG. 12 shows a nonlinear subfilter as used in FIG. 11 in greater detail.

FIG. 12 shows the subfilter 240 which corresponds with the subfilters 238, 236, 232, 234 in FIG. 11 in greater detail. Subfilter 240 is realized by using dynamic, linear and static, nonlinear elements. The input 242 of the subfilter 240 is connected via the linear filter 246 with the first input of a summer 256. The output of the filter 246 is also connected both with the inputs of the static nonlinearity 250 and the differentiator 248. The static nonlinearity 250 has a nonlinear relationship between the input and output as defined by Eq. (2). The outputs of 250 and 248 are connected with the inputs of a multiplier 252 and the output of the multiplier 252 is connected via the linear filter 254 with the second input of the summer 256. The output of summer 256 is connected to the output 244 of subfilter 240.

Figure 13:
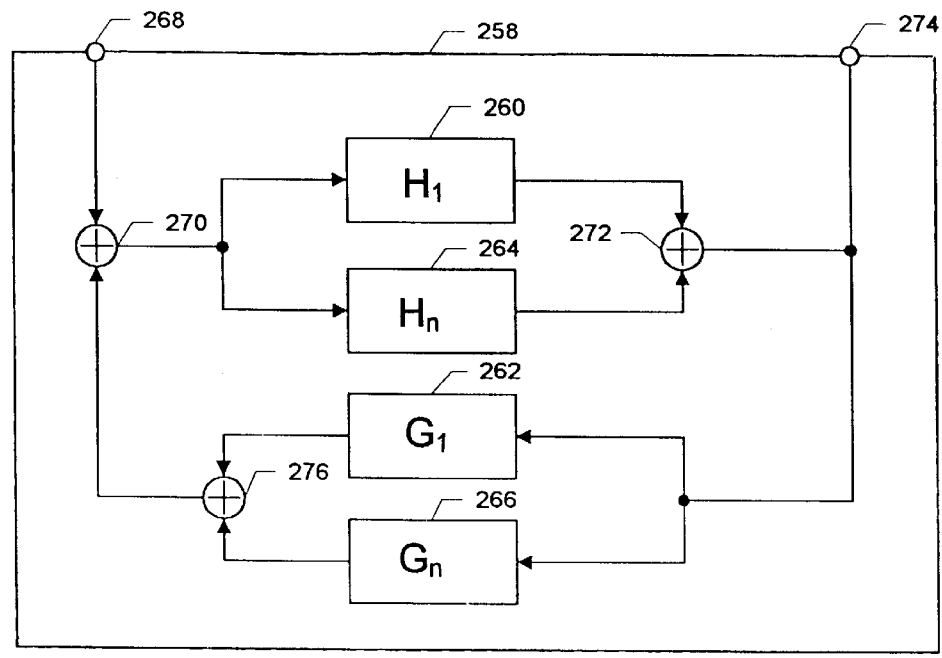
FIG. 13 shows the controller of FIG. 10 wherein each nonlinear filter comprises a linear and a nonlinear subfilter in parallel.

FIG. 13 shows an alternative embodiment 258 of the controller 212 in FIG. 10. Both nonlinear filters 218 and 220 are realized as a parallel connection of the linear filters 260 and 262 and nonlinear filters 264 and 266, respectively. The input 268 of the controller 258 is connected with the first input of a summer 270 which corresponds with summer 216 in FIG. 10. The output of summer 270 is connected with the inputs of the linear filter 260 and the nonlinear filter 264. The outputs of the filters 260 and 264 are connected via summer 272 with the output 274 of the controller 258. The output of the summer 272 is also connected with the inputs of the linear filter 262 and the nonlinear filter 266 in the upstream path. The outputs of the filters 262 and 266 are connected via summer 276 with the second input of summer 270.

Figure 14:
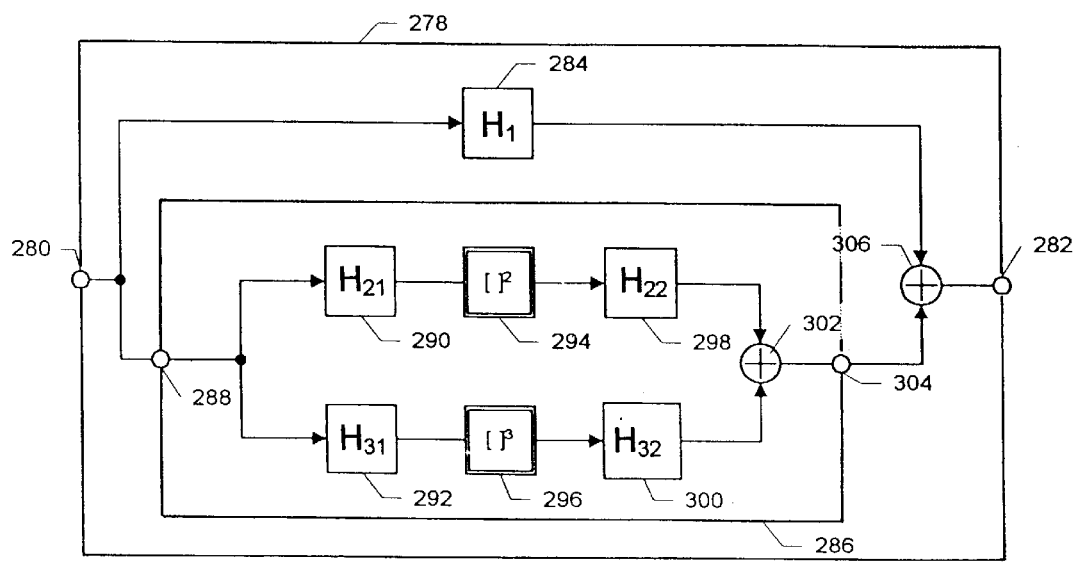
FIG. 14 shows a nonlinear filter with a $S_M$-structure.

FIG. 14 shows a nonlinear polynomial filter 278 which has a $S_M$-structure with M=3 and contains only dynamic linear and static nonlinear elements. It can be used to realize the nonlinear filters 218 and 220 in FIG. 10. The input 280 of the nonlinear filter 278 is connected both with the input of a linear subfilter 284 and with the input 288 of the nonlinear subfilter 286. The nonlinear filter 286 contains a second-order and third-order branch connected in parallel. In the second-order branch the input 288 is connected via the linear filter 290, via a squarer 294 and via a linear filter 298 with the first input of summer 302. In the third-order branch the input 288 is connected via the linear filter 292, via a third-order power unit 296, via a linear filter 300 with the second input of summer 302. The output of summer 302 is connected with the output 304 of the nonlinear subfilter 286. The outputs of the linear filter 284 and of the nonlinear subfilter 286 are connected via summer 306 with the output 282 of the nonlinear filter 278.

If the amplitude of the feedback sound radiated from loudspeaker 12 in upstream direction is negligible, the nonlinear filter 220 and the summer 216 in the feedback compensation of FIG. 10 can be omitted and the filter 278 with a $S_M$-structure replaces the controller 30 in FIG. 3.

Figure 15:
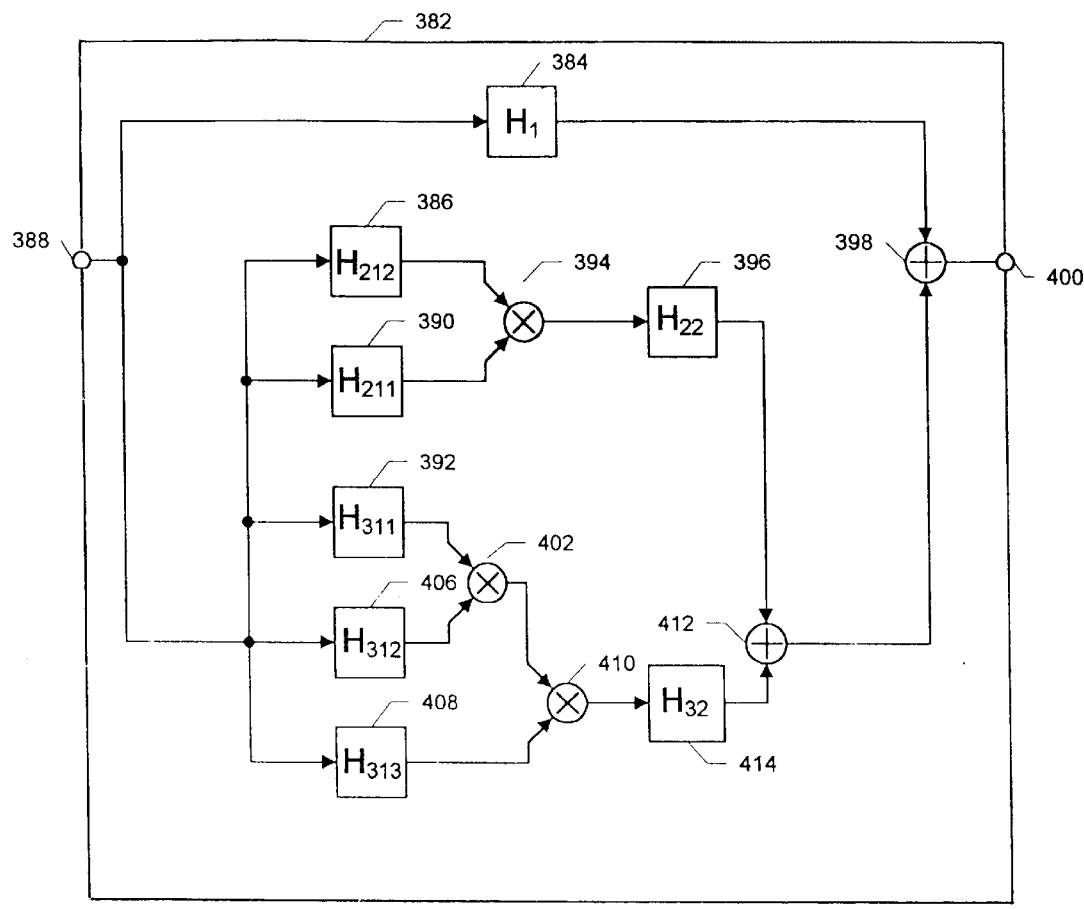
FIG. 15 shows a factorable polynomial filter.

FIG. 15 shows a factorable polynomial filter of third-order which can be used to realize the filters 218 and 220 in FIG. 10, alternatively. The filter input 388 comprises a linear, a second-order and a third-order path connected in parallel between the filter input 388 and filter output 400. The linear path contains only the linear filter 384 and the summer 398. In the second-order branch the filter input 388 is connected both via a first linear filter 386 with the first input of a multiplier 394 and via a second linear filter 390 with the second input of multiplier 394. The output of the multiplier 394 is connected with the input of another linear filter 396. In the third-order branch the input 388 is connected to three linear filters 392, 406, 408. The output of these filters is multiplied by using the multipliers 402 and 410 and supplied to the linear filter 414. The output signals of the linear filters 396, 384 and 414 are added by using summers 412 and 398 and supplied to the output 400.

Additional higher-order branches can be added to the polynomial filters 278 and 382 based on the VOLTERRA-series expansion truncated after the third-order term if compensation of higher-order distortions is required.

Figure 16:
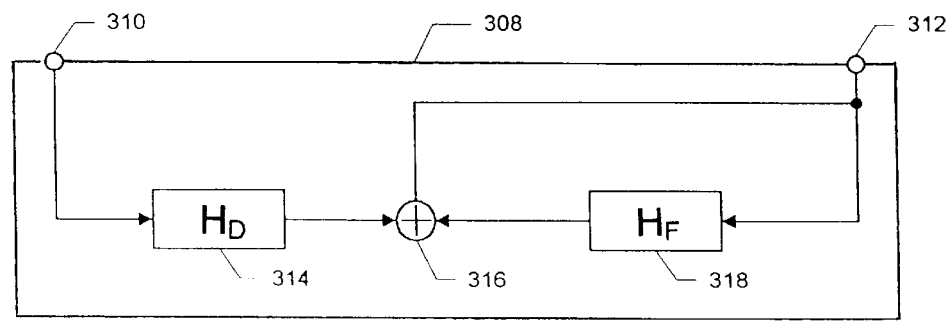
FIG. 16 shows a fourth embodiment of the nonlinear controller having a feedback and feed-forward path.

FIG. 16 shows a fourth embodiment of the nonlinear controller according to the invention. The controller 308 is derived from controller 258 in FIG. 13 and replaces the controller 30 in FIG. 3. The input 310 of the controller 308 which corresponds with input 50 in FIG. 3 is connected via filter 314 with the first input of summer 316. The output of summer 316 is connected with the output 312 of the controller 308 as well as via the filter 318 with the second input of summer 316. Both filters 314 and 318 have a $S_M$-structure as shown for filter 278 in FIG. 14. The linear filters 260, 262 and the nonlinear filters 264, 266 in FIG. 13 can be transformed either in filter 314 or filter 318 assuming that the amplitude of the nonlinear distortions is small in comparison to the fundamental sound and a nonlinear feedback structure can be approximated by a nonlinear feed-forward structure. There are different versions of the embodiment of this controller possible depending on the order of the nonlinear $S_M$-filters 314 and 318. Either the filter 314 or the filter 318 or both filters 314 and 318 are nonlinear. Transforming the feedback path completely into the feed-forward system 314 and omitting filter 318 has some drawbacks because linear filters with an infinite impulse response are required.

Figure 17:
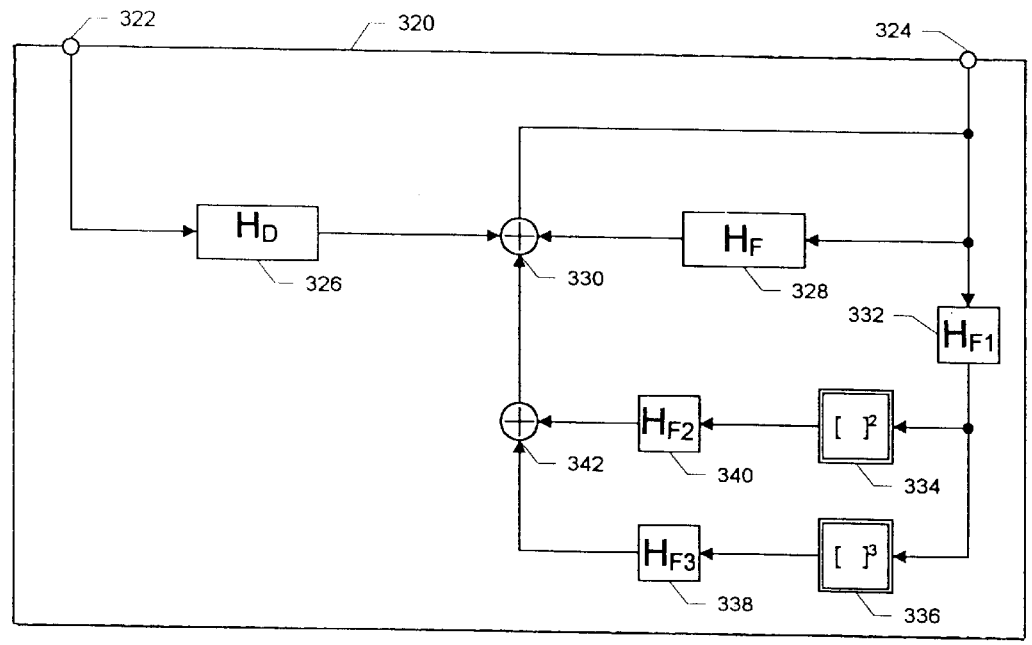
FIG. 17 shows the nonlinear controller of FIG. 16 using linear filters, a squarer, a third-order power unit and summers.

FIG. 17 shows a very efficient embodiment of the non-linear controller 308 in FIG. 16. The nonlinear filters 264 and 266 in FIG. 13 are transformed into the feedback path so that the controller input 322 is connected via the linear filter 326 with the first input of summer 330. The feedback path has a $S_M$-structure with M=3. Higher-order branches in the feedback path can be added if compensation for higher-order distortion is required. The output 324 is connected via the linear filter 328 with the second input of summer 330. The linear filters before the squarer 334 and the third-order power unit 336 have the same transfer response and are realized in FIG. 17 by only one linear filter 332. The output of the squarer 334 and third-order power device 336 are connected via the linear filters 340 and 338, respectively, via summer 342 and 330 with the output 324 of the controller.

Figure 18:
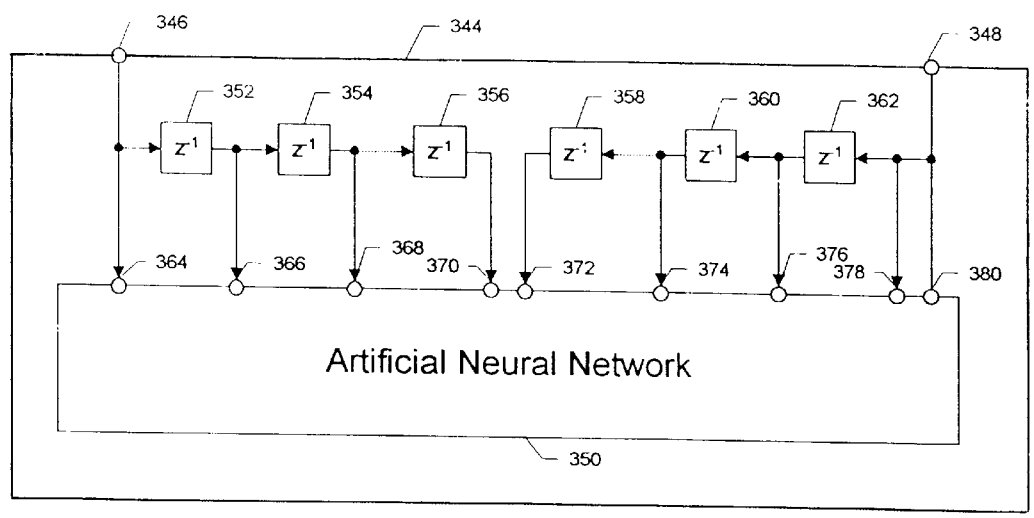
FIG. 18 shows a fifth embodiment of the nonlinear controller using a neural network and two delay lines.

FIG. 18 is a fifth embodiment 344 of the nonlinear controller according to the invention using a neural network 350. The neural network 350 is a three-layer perceptron as described in R. P. Lippmann, "An Introduction to Computing with Neural Nets," IEFE-ASSP Magazine, 1987, pp. 4–22. The inputs 364, 366, 368, 370, 372, 374, 376, 378 of the network 350 are connected trough adaptive weights with the first hidden nodes. The first hidden layer is connected via the second hidden layer with the output layer which is connected with the output 380 of the network. The input 346 of the controller 344 is connected with the input 364 of the network 350 as well as to the input of a first delay line comprising discrete delay elements 352, 354, 356. The output 380 of the neural network 350 is connected to the input 378 of the neural network 350 as well as to the input of a second delay line comprising the discrete delay units 362, 360, 358. Both delay line are tapped and the output of each delay unit 352, 354, 356, 358, 360, 362 is connected with the input 366, 368, 370, 372, 374, 376 of the network, respectively. The controller in FIG. 17 is a more formal embodiment of the invention and does not utilizes all the available a priori information about the nonlinear mechanisms in the acoustic system. However, the reflection and transmission of the upstream and downstream traveling waves and the interferences in the nonlinear distortion generation can be partly approximated. Due to the feedback path this controller has an infinite impulse response and can compensate for the feedback sound radiated by loudspeaker 2 to the microphone 8.

The invention may be embodied and practiced in other specific forms without departing from the spirit and essential characteristics thereof. The present embodiments are therefore to be considered in all respects as illustrative and not restrictive, the scope of the invention being indicated by the appended claims rather than by the foregoing description; and all variations, substitutions and changes which come within the meaning and range of equivalency of the claims are therefore intended to be embraced therein.

What is claimed is:

1. In an acoustic system having an input receiving high level input sound and an output radiating an unwanted output sound, an active attenuation method for attenuating said output sound, comprising the steps of:

sensing said input sound with an input transducer so as to derive therefrom a corresponding electric input signal;

injecting a canceling sound into said acoustic system by using an output transducer for converting an electric control signal into said canceling sound;

modeling the transfer characteristic of the input and output transducers;

modeling the nonlinear sound propagation of said input sound and said canceling sound in said acoustic system by dividing said acoustic system into a plurality of small acoustic sections;

modeling the nonlinear sound propagation in each said acoustic section by a lumped parameter model comprising dynamic, linear and static nonlinear elements;

generating said electric control signal from said electric input signal by using a nonlinear filter architecture which is derived from the modeling of the nonlinear sound propagation and from the modeling of the input and output transducers in a manner to compensate for nonlinearities in the acoustic system and to substantially attenuate said output sound through cancellation of said input sound by said canceling sound.

2. In an acoustic system having an input receiving high level input sound and an output radiating an unwanted output sound, an active attenuation method for attenuating said output sound, comprising the steps of:

sensing said input sound with an input transducer so as to derive therefrom a corresponding electric input signal;

injecting a canceling sound into said acoustic system by using an output transducer for converting an electric control signal into said canceling sound;

modeling the transfer characteristic of the input and output transducers;

modeling the nonlinear propagation of said input sound from said input transducer to the point where said input sound meets said canceling sound by a first nonlinear overall model; and modeling the nonlinear propagation of said canceling sound from said output transducer to said input transducer by a second nonlinear overall model;

modeling the nonlinear propagation of said canceling sound from said output transducer to the point where said canceling sound meets said input sound by a third nonlinear overall model; and separating in each said first, second and third nonlinear overall model a linear system which describes the transmission of a linear part from a nonlinear system which describes the generation of second-order or higher-order nonlinear distortions in said input sound and said canceling sound, whereas both said linear and nonlinear systems are connected in parallel;

generating said electric control signal from said electric input signal by using a nonlinear filter architecture which is derived from the modeling of the nonlinear sound propagation and from the modeling of the input and output transducers in a manner to compensate for nonlinearities in the acoustic system and to substantially attenuate said output sound through cancellation of said input sound by said canceling sound.

3. The active attenuation method as defined in claim 2 comprising modeling separately the generation of second- or higher-order nonlinear distortions by using a second- or higher-order homogeneous subsystem; and modeling each said second- or higher-order homogeneous subsystem by using dynamic, linear and static, nonlinear elements.

4. In an acoustic system having an input receiving high level input sound and an output radiating an unwanted output sound, an active acoustic attenuation arrangement for attenuating said output sound, comprising:

an input transducer sensing said input sound and providing therefrom an electric input signal;

an output transducer driven by an electric control signal and injecting a canceling sound into said acoustic system; and a nonlinear controller, having an sensing input supplied with said electric input signal and a controller output connected with said output transducer, whereas said electric control signal is derived from said electric input signal by simulating the nonlinear sound propagation in the acoustic system and by compensating for the linear or nonlinear transfer behavior of said input and output transducers to substantially attenuate said output sound through cancellation of said input sound by said canceling sound;

wherein said nonlinear controller comprises:

a nonlinear filter having a downstream input and a downstream output for modeling the nonlinear propagation of said input sound and having an upstream input and an upstream output for modeling the nonlinear propagation of a feedback sound radiated by said output transducer in upstream direction;

an inverter having an input connected to said downstream output and having an inverter output connected with said upstream input for providing an 180° phase shifted input signal;

an output filter having an input connected to the output of said inverter, having an output connected with said controller output and having a transfer characteristic between the input and output of said output filter such that the signal at the output of said inverter is equal to said cancelling sound in the acoustic system;

an input filter having an input connected to said sensing input and an output, the transfer characteristic between the input and output of said input filter being adjusted such that the signal at the output of said input filter is equal to the sum of said input sound and said feedback sound; and a summer having a noninverting input connected to the output of said input filter, an inverting input connected to the upstream output of the nonlinear filter and an output for providing said input sound to the downstream input of said nonlinear filter.

5. The active attenuation arrangement as defined in claim 4 wherein said nonlinear filter comprises a plurality of nonlinear subfilters, each of said nonlinear subfilters having a downstream input, a downstream output, an upstream input and an upstream output for modeling the nonlinear sound propagation in a section of the said acoustic system, said nonlinear subfilters in said nonlinear filter being connected in cascade by connecting the upstream output to the said upstream input and by connecting the downstream output to the downstream input of corresponding adjacent nonlinear subfilters, whereas the downstream input and the upstream output of the first nonlinear subfilter in the cascade and the downstream output and the upstream input of the last nonlinear subfilter in the cascade being connected with corresponding inputs and outputs of said nonlinear filter.

6. The active attenuation arrangement as defined in claim 5 wherein each of said nonlinear subfilters comprises:

a first summer having a first input connected to said downstream input, having a second input connected to said upstream output and having an output providing a total sound pressure signal;

a static nonlinearity having an input connected to the output of said first summer and having an output providing a signal which describes the nonlinearity of said acoustic system;

a differentiator having an input connected to said output of said first summer and having an output for providing a differentiated total sound pressure signal;

a multiplier having a first input connected with the output of said static nonlinearity, a second input connected with the output of said differentiator and an output providing a signal which corresponds with a nonlinear volume velocity component;

a linear filter having an input connected with the output of said multiplier and an output for providing a signal which corresponds with a nonlinear sound pressure component;

a second summer having a first input connected to the output of said linear filter, having a second input connected to the downstream input of said nonlinear subfilter and having an output providing a downstream traveling sound signal;

a third summer having a first input, having a second input connected with the output of said linear filter and having an output connected with said upstream output of said nonlinear subfilter;

a downstream transmission filter having an input connected to the output of said second summer and having an output providing a transmitted portion of the downstream traveling sound signal;

a downstream reflection filter having an input connected to the output of said second summer and having an output providing a portion of the downstream traveling sound signal which is reflected in upstream direction;

an upstream transmission filter having an input connected to said upstream input and having an output providing the transmitted portion of a signal at the upstream input;

an upstream reflection filter having an input connected to said upstream input and having an output providing a portion of a signal at the upstream input which is reflected in downstream direction;

a fourth summer having a first input connected to the output of said downstream transmission filter, having a second input connected to the output of said upstream reflection filter and having an output which is connected to said downstream output of said nonlinear subfilter; and a fifth summer having a first input connected to the output of said upstream transmission filter, having a second input connected to the output of said downstream reflection filter and having an output which is connected to the first input of said third summer.

7. The active attenuation arrangement as defined in claim 4 wherein said nonlinear filter comprises:

a nonlinear downstream filter having an input connected to said downstream input of said nonlinear filter and having an output connected with said downstream output of said nonlinear filter providing the distorted input sound in the acoustic system; and a nonlinear upstream filter having an input connected to the upstream input of said nonlinear filter and having an output connected with the upstream output of said nonlinear filter providing a signal which corresponds with the distorted feedback sound in the acoustic system.

8. The active attenuation arrangement as defined in claim 7 wherein each of both said nonlinear downstream filter and said nonlinear upstream filter comprises:

a linear subfilter having an input connected with the input of the filter and an output providing the filtered input signal;

a nonlinear subfilter having an input connected with the input of the filter and an output providing nonlinear distortions caused by nonlinear sound propagation in the acoustic system; and a summer having a first input connected with the output of said linear subfilter, a second input connected with the output of said nonlinear subfilter and an output connected with the output of the filter.

9. The active attenuation arrangement as defined in claim 4 wherein said output filter has a nonlinear transfer behavior between its input and output to compensate for the nonlinear sound propagation between the output transducer and the point where said canceling sound meets the downstream propagating input sound.

10. In an acoustic system having an input receiving high level input sound and an output radiating an unwanted output sound, an active acoustic attenuation arrangement for attenuating said output sound, comprising:

an input transducer sensing said input sound and providing therefrom an electric input signal;

an output transducer driven by an electric control signal and injecting a canceling sound into said acoustic system; and a nonlinear controller, having an sensing input supplied with said electric input signal and a controller output connected with said output transducer, whereas said electric control signal is derived from said electric input signal by simulating the nonlinear sound propagation in the acoustic system and by compensating for the linear or nonlinear transfer behavior of said input and output transducers to substantially attenuate said output sound through cancellation of said input sound by said canceling sound;

wherein said nonlinear controller comprises:

a summer having a first input connected with said sensing input of said nonlinear controller, a second input and an output providing the sum of the signals at the first and second input;

a downstream filter having an input connected with the output of said summer and an output connected to said controller output for modeling the nonlinear propagation of said input sound; and an upstream filter having an input connected with said controller output and an output connected to the second input of said summer for modeling the nonlinear propagation of said canceling sound in said acoustic system.

11. The active attenuation arrangement as defined in claim 10 wherein each of both said downstream filter and said upstream filter comprises:

a linear subfilter having an input connected with the input of the filter and an output providing the filtered input signal;

a nonlinear subfilter having an input connected with the input of the filter and an output providing nonlinear distortions to compensate for the nonlinearities in the acoustic system; and a summer having a first input connected with the output of said linear subfilter, a second input connected with the output of said nonlinear subfilter and an output connected with the output of the filter.

12. The active attenuation arrangement as defined in claim 10 wherein each of both said downstream filter and said upstream filter is a nth-order polynomial filter, comprising at least one ith-order homogenous filter ($1 \leq i \leq n$), whereas each said homogeneous filter having an input connected with the input of said polynomial filter and an output connected via a summer with the output of said polynomial filter.

13. The active attenuation arrangement as defined in claim 12 wherein said ith-order homogeneous filter with $i>1$ comprises a first linear filter having an input connected with the input of said homogeneous filter and an output providing the filtered input signal;

a ith-order power unit having an input connected with the output of said first linear filter and an output providing ith-order powered input signal; and a second linear filter having an input connected with the output of said ith-order power unit and having an output connected with the output of said homogeneous filter.

14. The active attenuation arrangement as defined in claim 12 wherein said ith-order homogeneous filter with $i>1$ comprises a plurality of i linear filters, whereas each of said i linear filters having an input connected with the input of said homogeneous filter and an output providing the filtered input signal;

a multiplier unit having i inputs connected with the output of said linear filters separately and an output providing the product of the output signals of said linear filters; and an additional linear filter having an input connected with the output of said multiplier unit and having an output connected with the output of said homogeneous filter.

15. The active attenuation arrangement as defined in claim 10 wherein each of both said downstream filter and said upstream filter comprises a plurality of nonlinear subfilters, each of said nonlinear subfilters having an input and an output, said nonlinear subfilters being connected in cascade by connecting the output and input of adjacent said nonlinear subfilters, the input and the output of the first and last nonlinear subfilter in the cascade being connected with corresponding input and output of the filter.

16. In an acoustic system having an input receiving high level input sound and an output radiating an unwanted output sound, an active acoustic attenuation arrangement for attenuating said output sound, comprising:

an input transducer sensing said input sound and providing therefrom an electric input signal;

an output transducer driven by an electric control signal and injecting a canceling sound into said acoustic system; and a nonlinear controller, having an sensing input supplied with said electric input signal and a controller output connected with said output transducer, whereas said electric control signal is derived from said electric input signal by simulating the nonlinear sound propagation in the acoustic system and by compensating for the linear or nonlinear transfer behavior of said input and output transducers to substantially attenuate said output sound through cancellation of said input sound by said canceling sound;

wherein said nonlinear controller comprises:

a summer having a first input, a second input and an output connected to said controller output providing the sum of the signals at the first and second input;

a first filter having an filter input connected with said sensing input of said nonlinear controller and an filter output connected with the first input of said summer forming a feed-forward path; and a second filter having an filter input connected with the output of said summer and an filter output connected to the second input of said summer forming a feedback path, either said first filter or said second filter or both said first filter and said second filter have a nonlinear transfer characteristic between the filter input and the filter output.

17. The active attenuation arrangement as defined in claim 16 wherein each of both said first filter and said second filter is a nth-order polynomial filter, comprising at least one ith-order homogenous filters ($1 \leq i \leq n$), whereas each said homogeneous filter having an input connected with the input of said polynomial filter and an output connected via a summer with the output of said polynomial filter.

18. The active attenuation arrangement as defined in claim 17 wherein said ith-order homogeneous filter with i>1 comprises a first linear filter having an input connected with the input of said homogeneous filter and an output providing the filtered input signal;

a ith-order power unit having an input connected with the output of said first linear filter and an output providing ith-order powered input signal; and a second linear filter having an input connected with the output of said ith-order power unit and having an output connected with the output of said homogeneous filter.

19. The active attenuation arrangement as defined in claim 17 wherein said ith-order homogeneous filter with i>1 comprises:

a plurality of i linear filters, whereas each of said i linear filters having an input connected with the input of said homogeneous filter and an output providing the filtered input signal;

a multiplier unit having i inputs connected with the output of said linear filters separately and an output providing the product of the output signals of said linear filters; and an additional linear filter having an input connected with the output of said multiplier unit and having an output connected with the output of said homogeneous filter.

20. The active attenuation arrangement as defined in claim 16 wherein said second filter comprises:

a linear subfilter having an input connected with the input of said second filter and an output providing the filtered input signal;

a nonlinear subfilter having an input connected with the input of said second filter and an output providing nonlinear distortions caused by nonlinearities in the acoustic system; and a summer having a first input connected with the output of said linear subfilter, a second input connected with the output of said nonlinear subfilter and an output connected with the output of said second filter.

21. The active attenuation arrangement as defined in claim 20 wherein said nonlinear subfilter comprises a first linear filter having an input connected with the input of said nonlinear subfilter and an output providing the filtered input signal; and a second summer having at least two inputs and an output connected with the output of said nonlinear subfilter; and at least two homogeneous filters of different order, whereas each homogeneous filter having an input connected with the output of said first linear filter and an output connected via said second summer with the output of said nonlinear subfilter; and each said homogeneous filter of ith-order with i>1 contains a ith-order power unit having an input connected with the input of said homogeneous filter and an output connected via an additional linear filter with the output of said homogeneous filter.

22. In an acoustic system having an input receiving high level input sound and an output radiating an unwanted output sound, an active acoustic attenuation arrangement for attenuating said output sound, comprising:

an input transducer sensing said input sound and providing therefrom an electric input signal;

an output transducer driven by an electric control signal and injecting a canceling sound into said acoustic system; and a nonlinear controller, having an sensing input supplied with said electric input signal and a controller output connected with said output transducer, whereas said electric control signal is derived from said electric input signal by simulating the nonlinear sound propagation in the acoustic system and by compensating for the linear or nonlinear transfer behavior of said input and output transducers to substantially attenuate said output sound through cancellation of said input sound by said canceling sound;

wherein said nonlinear controller comprises:

a feed-forward tapped delay line, comprising a plurality of n delay elements connected in series, having an input connected to said sensing input and providing a set of n+1 progressively delayed signal outputs;

a feedback tapped delay line, comprising a plurality of m delay elements connected in series, having an input connected to said controller output and providing a set of m+1 progressively delayed signal outputs; and a neural network having a plurality of m+n+2 inputs connected respectively to the signal outputs of said feed-forward tapped delay line and said feedback tapped delay line, having an output connected to said controller output.

* * * * *